United States Patent
DiFoggio et al.

(10) Patent No.: US 7,346,460 B2
(45) Date of Patent: Mar. 18, 2008

(54) DOWNHOLE PV TESTS FOR BUBBLE POINT PRESSURE

(75) Inventors: Rocco DiFoggio, Houston, TX (US); John M. Michaels, Cypress, TX (US); Jaedong Lee, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 159 days.

(21) Appl. No.: 10/872,713

(22) Filed: Jun. 21, 2004

(65) Prior Publication Data

US 2004/0260497 A1    Dec. 23, 2004

Related U.S. Application Data

(60) Provisional application No. 60/480,149, filed on Jun. 20, 2003.

(51) Int. Cl.
*G01F 17/00* (2006.01)
*E21B 49/08* (2006.01)

(52) U.S. Cl. .................... 702/50; 73/152.27

(58) Field of Classification Search ............ 702/98, 702/99, 50; 73/37, 152.27, 152.18–152.19, 73/152.22–152.23; 703/9, 10
See application file for complete search history.

(56) References Cited

U.S. PATENT DOCUMENTS

| | | | | |
|---|---|---|---|---|
| 4,782,695 A | | 11/1988 | Glotin et al. | 73/152.18 |
| 4,860,581 A | | 8/1989 | Zimmerman et al. | 73/152.26 |
| 4,936,139 A | | 6/1990 | Zimmerman et al. | 73/152.26 |
| 5,303,775 A | | 4/1994 | Michaels et al. | 166/264 |
| 5,377,755 A | | 1/1995 | Michaels et al. | 166/264 |
| 5,473,939 A | * | 12/1995 | Leder et al. | 73/152.12 |
| 5,549,159 A | | 8/1996 | Shwe et al. | 166/250.02 |
| 5,602,334 A | * | 2/1997 | Proett et al. | 73/152.05 |
| 5,635,631 A | | 6/1997 | Yesudas et al. | 73/61.46 |
| 5,644,076 A | * | 7/1997 | Proett et al. | 73/152.41 |
| 6,061,634 A | * | 5/2000 | Belani et al. | 702/12 |
| 6,101,447 A | * | 8/2000 | Poe, Jr. | 702/13 |

(Continued)

FOREIGN PATENT DOCUMENTS

EP    0395200 A1    10/1990

(Continued)

OTHER PUBLICATIONS

Temperley, H.N.V., The Behavior of Wwater Under Hydrostatic Tension: III, Aug. 1946, pp. 199-208.*

(Continued)

*Primary Examiner*—John Barlow
*Assistant Examiner*—Toan M. Le
(74) *Attorney, Agent, or Firm*—Madan, Mosmsan & Sriram, P.C.

(57) ABSTRACT

The present invention provides an objective bubble point pressure determination method enables new applications of downhole PV (Pressure Volume) test results such as in situ measurement of the bubble point pressure for use as a quality control parameter for sampling. The present invention provides a method and apparatus to fit data points to a curve and to smooth these points over an interval of N points. The derivative of the curve is determined to obtain peak acceleration. The peak acceleration represents the bubble point pressure. This bubble point pressure is verified by comparison to changes in fluid compressibility and visual observation of a pressure volume plot history.

29 Claims, 10 Drawing Sheets

U.S. PATENT DOCUMENTS

| | | | |
|---|---|---|---|
| 6,108,608 A * | 8/2000 | Watts, III | 702/30 |
| 6,250,138 B1 | 6/2001 | Shwe et al. | 73/64.54 |
| 6,274,865 B1 | 8/2001 | Schroer et al. | 250/269.1 |
| 6,334,489 B1 * | 1/2002 | Shwe et al. | 166/250.01 |
| 6,350,986 B1 | 2/2002 | Mullins et al. | 250/269.1 |
| 6,474,152 B1 | 11/2002 | Mullins et al. | 73/152.22 |
| 6,490,916 B1 * | 12/2002 | Goodwin et al. | 73/152.58 |
| 6,502,634 B1 | 1/2003 | Evans et al. | 166/250.03 |
| 6,568,487 B2 * | 5/2003 | Meister et al. | 175/50 |
| 6,672,386 B2 * | 1/2004 | Krueger et al. | 166/252.5 |
| 6,714,872 B2 * | 3/2004 | DiFoggio et al. | 702/12 |
| 6,748,328 B2 * | 6/2004 | Storm et al. | 702/6 |
| 6,923,052 B2 * | 8/2005 | Krueger et al. | 73/152.22 |
| 6,941,804 B2 * | 9/2005 | Hasem et al. | 73/152.24 |
| 7,107,188 B2 * | 9/2006 | Veneruso et al. | 702/187 |
| 2002/0117299 A1 | 8/2002 | Haugland et al. | 166/254.2 |
| 2002/0134587 A1 | 9/2002 | Rester et al. | 175/48 |
| 2003/0182061 A1 * | 9/2003 | Ferworn et al. | 702/12 |
| 2004/0000400 A1 | 1/2004 | Fujisawa et al. | 166/250.1 |
| 2004/0133350 A1 * | 7/2004 | Veneruso et al. | 702/6 |

FOREIGN PATENT DOCUMENTS

| | | |
|---|---|---|
| EP | 0610098 A1 | 8/1994 |
| GB | 2304906 A | 3/1997 |

OTHER PUBLICATIONS

Almehaideb et al., EOS Tuning to Model Full Field Crude Oil Properties Using Multiple Well Fluid PVT Analysis, 2000, Journal of Petroleum Science and Engineering 26, pp. 291-300.*

Elsharkawy, Adel, An Empirical Model for Estimating the Saturation Pressures of Crude Oils, 2003, Journal of Petroleum Science and Engineering 38, pp. 57-77.*

Cinco-Ley et al., Analysis of Pressure Tests Through the Use of Instantaneous Source Response Concepts, 1986, SPE 15476.*

Deruyck et al., Testing Design and Analysis, Apr. 1992, Oilfield Review, pp. 28-45.*

Lee et al., Fluid Sampling From Damaged Formations, SPE 39817, 1998, pp. 565-570.

Sarkar et al., Adverse Effects Of Poor Mud Cake Quality: A Supercharging And Fluid Sampling Study, SPE 48958, 1998, pp. 1-12.

Mullins et al., Real-Time Quantification Of OBM Filtrate Contamination During Openhole Wireline Sampling By Optical Spectroscopy, SPWLA 41st Annual Logging Symposium, Jun. 4-7, 2000, pp. 1-10.

* cited by examiner

*FIG. 1*

Downhole bubble point test

*FIG. 2*

Determination of bubble point pressure using the interval-by-interval Second Derivative Method showing a plot of each interval's fitting coefficient vs. pressure.

*FIG. 3*

Changes in Fluid Compressibility

FIG. 4

Pressure - Volume plot.
The bubble point pressure is determined through combination fo second derivative, compressibility, and the curve fit.

FIG. 5

Pressure and volume history plot for a pumping job

FIG. 6

FRA plot for the pumping data.
FRA mobility and fluid compressibility are calculated.

Second PVT test after 1.65 liters of pumping.
Estimated bubble point pressure is 15248 psi

FIG. 7

Fourth PVT test after 11.1 liters of pumping
Estimated bubble point pressure is 15510 psi

| Variable | PVTMod | Meas. Data |
|---|---|---|
| Reservoir Fluid MW | 35 | 34.1 |
| Single Stage GOR | 5825 | 6760 |
| Reservoir Fluid Density | 0.49 | 0.488 |
| Reservoir SSPVF | | |
| Reservoir Fluid Viscosity | 0.1 | 0.10 |
| Saturation Pressure | 10459 | 8361 |
| Saturated Fluid Density | 0.46 | 0.47 |
| Saturated SSPVF | | |
| API Gravity | 39.4 | 38.5 |
| STO Sulfer Content | 0.53 | 0.5 |
| Reservoir Fluid N2 | 0.4 | 0.37 |
| Reservoir Fluid CO2 | 0.2 | 0.21 |
| Reservoir Fluid C1 | 80.1 | 79.49 |
| Reservoir Fluid C2 | 4.9 | 4.08 |
| Reservoir Fluid C3 | 2.7 | 3.09 |
| Reservoir Fluid iC4 | 0.7 | 0.76 |
| Reservoir Fluid nC4 | 1.2 | 1.55 |
| Reservoir Fluid iC5 | 0.5 | 0.71 |
| Reservoir Fluid nC5 | 0.6 | 0.88 |
| Reservoir Fluid C6 | 1.1 | 1.29 |
| Reservoir Fluid C7+ | 7.5 | 7.57 |
| Reservoir Fluid C7+ MW | 220 | 228.20 |
| Reservoir Fluid C7+ SG | 0.81 | 0.805 |
| Flash Gas Gravity | 0.72 | 0.725 |
| Gross Heating Value | 1279 | 1268 |

FIG. 9

Comparison of fluid properties from the PVT$^{MOD}$ and laboratory analysis

DOWNHOLE PV TESTS FOR BUBBLE POINT PRESSURE

CROSS REFERENCE TO RELATED APPLICATIONS

This patent application claims priority from U.S. patent application Ser. No. 60/480,149 filed on Jun. 20, 2003 entitled "Improved Downhole PV Tests for Bubble Point Pressure" by Rocco DiFoggio, Jaedong Lee and John Michaels.

BACKGROUND OF THE INVENTION

1. Field of the Invention

The present invention relates to the field of downhole formation fluid sampling and in particular to the determination of bubble point pressure for a fluid down hole.

2. Background of the Related Art

A primary function of a wireline formation fluid sampling and testing tool, such as the Reservoir Characterization Instrument (RCI™) provided by Baker Atlas, is to collect multiple reservoir fluid samples to evaluate potentially productive reservoir units.

These collected fluid samples are brought to an onshore laboratory facility for PVT (Pressure, Volume, Temperature) and compositional analysis. It is important to obtain high quality samples, which can be used with confidence to predict reservoir behavior. The sample quality depends on the contamination level and the sampling pressure relative to the reservoir bubble point pressure. If the contamination is low (less than 10% by volume), and the sample was taken and maintained above bubble point pressure, then the sample is considered to be very high quality.

If the sample is not collected and subsequently maintained above bubble point pressure, then asphaltenes (heavy components) will fall out of solution just below the fluid's bubble point pressure. Once out of solution, it is unlikely that asphaltenes can be recombined back into the oil, so the fluid properties are permanently altered.

This problem is particularly important for deepwater exploration. If a non-representative sample is used to determine fluid properties, then during production asphaltenes may unexpectedly come out of solution near the wellbore or in the marine riser or the production pipelines. However, when the true formation fluid properties are accurately known based on a high-quality fluid sample, such potential problems can be reduced or eliminated. For an exploration well, for which no samples were recovered, having measured bubble point pressures can be of considerable value in planning the development of the reservoir.

The current generation formation testers are able to measure the bubble point pressure ($P_b$,) of a formation fluid at the time of sample collection. These testers trap a volume of fluid and gradually expand that volume and monitor how the pressure drops. Initially, the pressure drops linearly with expanding volume. The estimated bubble point pressure is the first pressure at which pressure is no longer linearly related to volume. Because the RCI™ pump provides a linear position digitizer on the pump shaft, the RCI™ operator equipment directly measures the volume change and records the corresponding pressure using a quartz gauge. Because RCI™ performs downhole bubble point pressure measurements in the same way that surface laboratories do (by monitoring P versus V), the downhole bubble point pressure measurements correlates well to laboratory measurements. See, e.g., Kasap, E., Huang, K., Shwe, T. and Georgi, D.: "Formation-Rate-Analysis Technique: Combined Drawdown and Buildup Analysis for Wireline Formation Test Data," SPEREE, June 1999, Vol 2, No. 3, 273.

The capability to perform the downhole bubble point test was introduced some time ago in Michaels, J., Moody, M., and Shwe, T.: "Advances in Wireline Formation Testing," paper presented at the 1995 SPWLA Annual Logging Symposium, Paris, France, Jun. 26-29, 1995, but in practice, information from the bubble point pressure test is subjective and not as accurate or repeatable as desired. Thus there is a need for an objective repeatable bubble point pressure test.

SUMMARY OF THE INVENTION

The present invention provides an objective repeatable bubble point pressure determination method which enables new applications of downhole PV (Pressure Volume) test results such as in situ measurement of the bubble point pressure for use as a quality control parameter for sampling. The present invention provides a method and apparatus to fit data points to a curve and to smooth these points over an interval of N data points. The pressure versus volume curve is monitored to detect a transition between a gradual slope and a relatively steep slope to determine bubble point pressure by visual observation. The derivative of this smoothed curve is then analyzed to determine its peak acceleration. The peak acceleration represents the bubble point pressure. This bubble point pressure is verified by comparison to changes in fluid compressibility and visual observation of a pressure volume curve. An optimal pump rate is selected to stay above the bubble point pressure. Formation clean up and reduction of filtrate from a formation fluid or a fluid sample are determined by monitoring compressibility for the fluid or fluid sample.

BRIEF DESCRIPTION OF THE FIGURES

For detailed understanding of the present invention, references should be made to the following detailed description of the exemplary embodiment, taken in conjunction with the accompanying drawings, in which like elements have been given like numerals, wherein.

DETAILED DESCRIPTION OF A EXEMPLARY EMBODIMENT

The following nomenclature is used in the following detailed description:
k Permeability, L$^{-2}$.
P Pressure, (pounds per square inch (psi). (M/LT$^2$)
q Volumetric flow rate, L$^3$/T.
r Radius, cm.
G$_o$ Geometric factor, 1/L.
c$_t$ Compressibility, (M/LT$^2$)$^{-1}$
V$_{sys}$ Volume of tool system, L$^3$.

Figure 1:
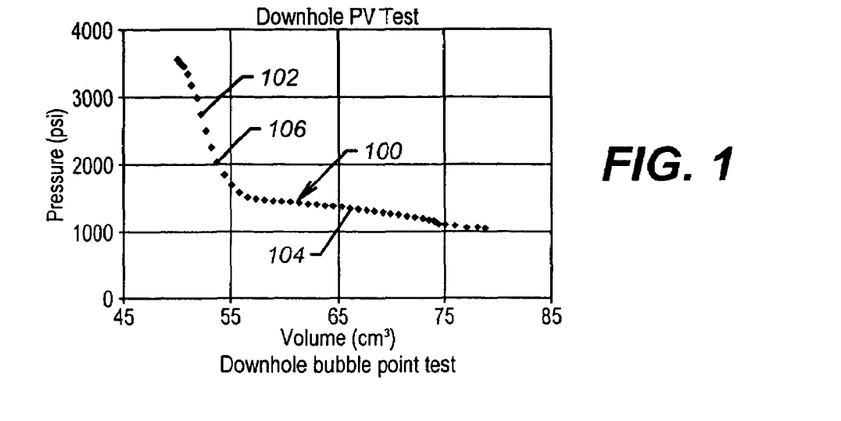
FIG. 1 is a plot of data points for a pressure versus volume downhole PV test.

Turning now to FIG. 1, the shape of a pressure versus volume plot 100 is a steeply sloping line 102, followed by a gently sloping line 104. The bubble point pressure is the pressure at which the steeply sloping line first curves upward 106.

Traditionally bubble point has been estimated from such curves visually. Visual interpretation is by nature subjective, rather than objective and thus necessarily variant and difficult to produce repeatable results between wells or samples taken in the same well. The present invention provides a novel automated method and apparatus, providing an objection which removes subjectivity and is much more repeatable. The present invention is useful for downhole testing as well as PVT testing performed at the surface in a PVT laboratory. It is recommended that the speed at which the pressure varies during a test be consistent so that results between tests are more consistent. In one embodiment of the invention, all tests are performed by varying the pressure at the same rate or speed to facilitate consistent results between tests. In one example of the invention, the pressure is varied slowly and consistently to minimize any variations in temperature due to changes in pressure. In another example of the invention, the temperature and pressure are stabilized by waiting an appropriate time after each change in pressure to allow the temperature and pressure to stabilize.

One of the difficulties, however, in trying to use such an automated objective method and apparatus is noise in the data. There is no single function that fits the entire curve from which we can estimate the point of greatest upward acceleration away from the initial downward sloping line. Instead, the present invention uses a rolling series of fits to a quadratic or cubic equation. A fit preferably covers an interval of N neighboring points. The next fit, moves over by one point and covers the next N-point interval.

The functional form of the curve being used for the fitting is defined and known, thus the first and second derivatives for the curve can be determined analytically. For example, if the fitting function is, Y=ax$^2$+bx+c, then, its second derivative, which is the "acceleration" away from the initial downward sloping line 102 is, d$^2$Y/dx$^2$=2a.

Figure 2:
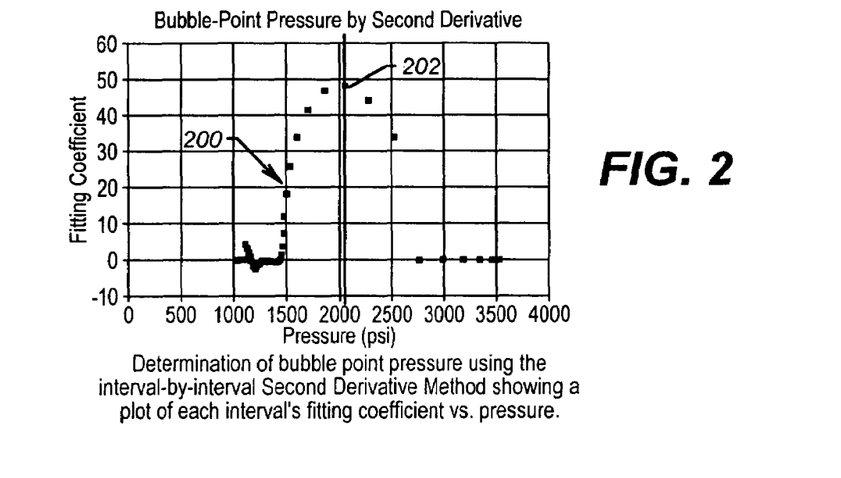
FIG. 2 is a plot of data points for determination of bubble point pressure using an interval-by-interval second derivative method showing a plot of each interval's fitting coefficient versus pressure.

As shown in FIG. 2, plotting the fitting coefficients "a" for each interval versus the volume at the center of each interval, a curve 200 with a peak 202 in it is obtained. The peak 202 is the bubble point pressure.

Figure 3:
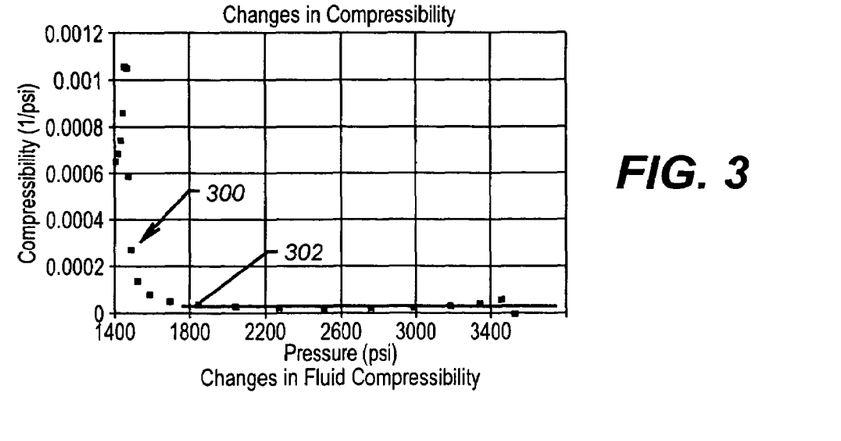
FIG. 3 is a plot of data points for compressibility versus pressure showing changes in fluid compressibility, which indicates fluid bubble point pressure.

When there are only a few data points in the downhole PV test, the above mentioned second derivative method yields slightly different results depending on the number of points, N, in the fitting interval. In such a case, changes in fluid compressibility can be used in conjunction with the second derivative method to pick the bubble point pressure. A simple stepwise compressibility is calculated by $$c_t = -\frac{1}{V}\frac{\Delta V}{\Delta P},$$

where V is the test chamber volume, $\Delta V$ is the incremental volume change, and $\Delta P$ is the decrease in pressure 302. FIG. 3 shows the compressibility values 300 for the same data.

Figure 4:
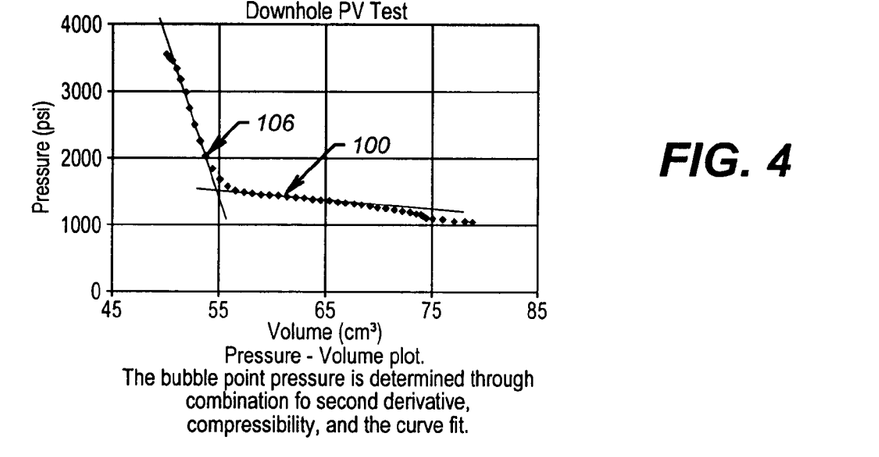
FIG. 4 is a plot of data points for a pressure versus volume downhole PV test in which the bubble point pressure is determined through combination of second derivative, compressibility, and a curve fit to the data points.

As shown in FIG. 4, these two methods can be verified by a third method: visual inspection of the pressure-volume plot 100. Using the values from the two methods, a slope can be drawn to fit the liquid part of the data. The combination of all three methods gives increased confidence in the bubble point pressure determination and enables the measurement to be used to insure that a high quality sample is being obtained.

With current generation formation testers, the bubble point pressure (P$_b$) of a formation fluid is measured in real-time time during downhole sample collection. Although detection of bubbles in a fluid is possible by passing light through the fluid, this approach is compromised whenever particulates are present in the fluid. Instead, a known volume of formation fluid is trapped and the pressure measure as the volume is gradually increased at an approximately constant downhole temperature. From a plot of pressure versus volume, the present invention determines P$_b$, as that point where the pressure accelerates fastest away from its initial linear trend. This entire procedure takes two to five minutes.

Estimating P$_b$, visually from the pressure-volume plot is subjective and produces too much variance in P$_b$. The present example of the invention provides a unique method and apparatus for processing P versus V data to find P$_b$. The present invention eliminates human bias and so reduces uncertainty in P$_b$. With increased confidence in the downhole bubble point pressure, the present invention uses calculations based on the measured P$_b$, as a quality control parameter to insure collecting a high quality sample.

The unstable nature of an open hole requires pumping fluid from the formation as quickly as possible to minimize the risk of sticking the tool in the wellbore or losing the well. However, if the pressure is drawn down below the bubble point during pumping, a sampling tool will collect a non-representative "flashed" sample. By measuring the bubble point pressure during the pumping a sample from the formation, an optimal pump rate is determined so that samples can be pumped at the fastest rate that does not cause the flowing pressure to drop below the bubble point pressure and thus insures that the sample does not phase separate.

In wells drilled using an oil-based mud, successive downhole PV tests while pumping show that the bubble point pressure rises as the filtrate contamination falls so we can also use P$_b$, from consecutive tests as a formation clean-up indicator.

As shown in FIG. 1, from left to right, the pressure versus volume plot 100 shows a smooth transition from a steeply sloping line 102 to a gently sloping line 104. The bubble point pressure is the pressure at which the steeply-sloping line begins transition to gently sloping line. Traditionally, an operator visually estimated bubble point pressure from such curves. Visual estimation of $P_b$ from the pressure-volume plot is highly subjective and produces too much variance in the reported $P_b$. Thus the present invention reduces the uncertainty of $P_b$ and eliminates human bias.

One of the difficulties in trying to use an automated procedure as provided in the present invention is noise in the data. Also, there is no single function that fits the entire P-V curve, which could then be used to estimate the point of fastest transition away from the initial downward sloping line. Instead, the present invention uses a quadratic or cubic equation to fit a rolling series of intervals along the P-V curve.

This fit covers an interval of N neighboring points. Then, the next fit moves over by one point and covers the next N-point interval as shown in FIG. 13. The number of points in an interval is chosen to be large enough to average out noise in the data. This method also eliminates the conceptual bias of requiring that a data interval be fit to a straight line.

Because we define the functional form of the curve that we use for the fitting, we can calculate analytically its first and second derivatives. For example, for a quadratic fit, our fitting function is, $P=aV^2+bV+c$, so its second derivative is the "acceleration," $d^2P/dV^2=2a$, from the initial downward-sloping line. Plotting each interval's least-squares-fit coefficient, a, against the corresponding midpoint pressure of that interval, the present invention plots a curve with a peak. In this case the peak is both the local and global extreme value. Other localized maxima and minima may also yield another fluid property. An extremum is either a maximum or minimum point of a curve and can be local or global. As shown in FIG. 2, which plots fitting coefficients versus interval-midpoint pressures for the data of FIG. 1, this peak is a good indicator of bubble point pressure. In FIG. 2, it indicates that the bubble point pressure 202 for the fluid is 2042 psi.

When there are not many data points in the downhole PV test, the second derivative method yields slightly different results depending on the number of points, N, in the fitting interval. In such a case, changes in fluid compressibility can be used in conjunction with the second derivative method to pick the bubble point pressure. A simple stepwise compressibility is calculated by $$c_t = -\frac{1}{V}\frac{\Delta V}{\Delta P},$$

where V is the test chamber volume, $\Delta V$ is the incremental volume change, and $\Delta P$ is the decrease in pressure. FIG. 3 shows the compressibility values for the data. The baseline compressibility is $2.5\times10^{-5}$ (1/psi), and it begins to go up 302 at the pressure of 2042 psi. Here, we see that the second derivative method and compressibility change method indicate the same pressure for the bubble point.

These two methods can be verified by a third method: visual inspection of the pressure-volume plot. Using the values from the two methods, a slope is drawn to fit the liquid part of the data as shown in FIG. 4. In FIG. 4, the straight line fit shows that the pressure-volume relationship begins to deviate after 2042 psi 106. The combination of all three methods gives increased confidence in the bubble point pressure determination and allows the measurement to be used to insure that a high quality sample is being obtained.

The present invention enables improved applications, for example, single phase pumping during sampling operations. The dynamic nature of an open hole requires pumping fluid from the formation as quickly as possible. When the mud cake is not completely sealed, faster pumping recovers better quality samples. See, Sarkar, A. K., Lee, J., and Kasap, E.: "Adverse Effects of Poor Mudcake Quality: A Supercharging and Fluid Sampling Study," SPEREE, June 2000, Vol. 3, No.3, 256-262. For this reason, pumping at the highest permissible pump rate meets the need for obtaining a high quality sample. However, if the flowing pressure is drawn below the bubble point pressure while pumping, a non-representative "flashed" sample is recovered. Once the pumping pressure becomes less than the bubble point pressure, some gas component is flashed and accumulated at the near well bore region until it reaches a critical gas saturation. Hence, the fluid flowing into the tool is no longer representative of the true formation fluid. Measuring the bubble point pressures during the pumping and maintaining the flowing pressure above the estimated bubble point pressure insures that the sample has not undergone phase separation.

Even after collecting a fluid sample in a sealed tank, phase separation can occur if the pressure in the tank falls too low because of shrinkage of the sample volume as the temperature falls upon return to the surface. Recently, considerable attention has been paid to the pressure history of collected reservoir fluids and pressure maintenance is now believed to be one of the most important parameters influencing sample quality. A system to control the sample pressure, such as a pressure-compensated sample tank, was described recently by Shammai, M., Shaw, A., DiFoggio, D., Gordon, B., Ferworn, K., and Ford, J.: "Improving Formation Sampling and Testing Efficiency—Tomorrow's In-situ PVT Laboratory," paper presented at 14th Annual Deep Offshore Technology International Conference, Nov. 13-15. (2002) which is hereby incorporated by reference in its entirety. See also, Kasap, E., Huang, K., Shwe, T. and Georgi, D.: "Formation-Rate-Analysis Technique: Combined Drawdown and Buildup Analysis for Wireline Formation Test Data," SPEREE, June 1999, Vol 2, No. 3, 273 which is hereby incorporated by reference in its entirety. See also, U.S. Provisional Patent application 60/464,917 filed on Apr. 23, 2003 by M. Shammai and J. Lee, entitled "A Method and Apparatus for Pumping Quality Control Through Formation Rate Analysis Techniques" which hereby incorporated by reference herein in its entirety; and U.S. Provisional Patent application No. 60/453,316 filed on Mar. 10, 2003 by M. Shammai and J. Lee, entitled "A Method and Apparatus for Pumping Quality Control Through Formation Rate Analysis Techniques" which is hereby incorporated by reference herein in its entirety.

The system calculates the necessary amount of overpressure along with the volume of nitrogen required in the pressure-compensated sample tank to keep the sample pressure above the estimated bubble point pressure.

Figure 5:
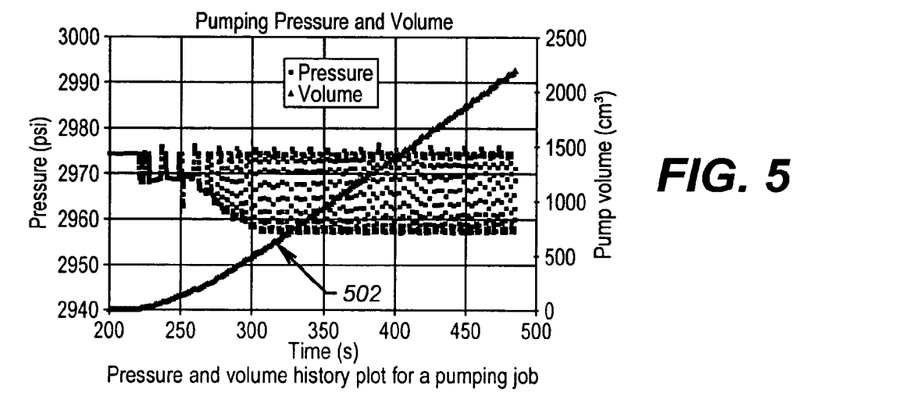
FIG. 5 is pressure and volume history plot for a pumping job.
Figure 6:
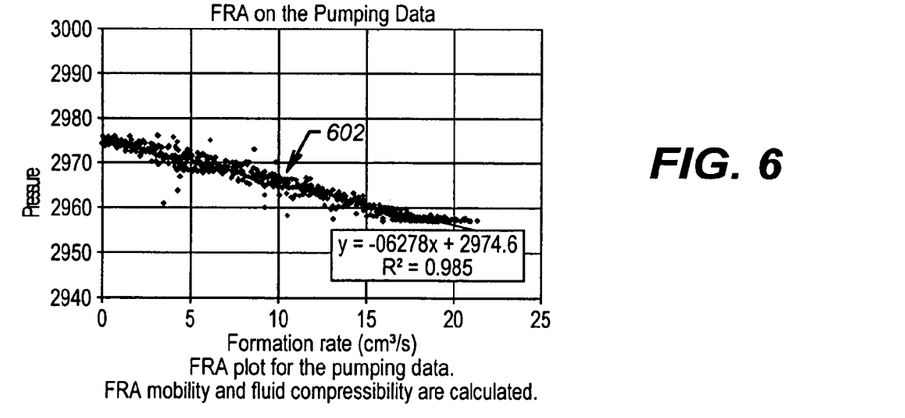
FIG. 6 is a Formation Rate Analysis (FRA) plot for the pumping data, wherein FRA mobility and fluid compressibility are calculated.

Formation Rate Analysis ($FRA^{SM}$) has been used to analyze pressure data from a formation tester Lee, J. and Michaels, J: "Enhanced Wireline Formations Tests in Low-Permeability Formations: Quality Control Through Formation Rate Analysis," SPE 60293, paper presented at the 2000 SPE Rocky Mountain Regional/Low Permeability Reservoirs Symposium, Denver, Colo., 12-15 Mar. 2000 which is hereby incorporated by reference in its entirety. FRA is applied to pressure data analysis by calculating the formation flow rate using the piston draw down rate compensated by the fluid compressibility effect. FRA is, in principle, applicable to the pumping data when the pump volume is available. FRA analysis on pumping data provides the formation mobility and works as a quality indicator for the pumping process. FIG. 5 shows a portion of pump pressure and volume history 502. The plot shows that 2.2 liters were pumped over 450 seconds. The results of applying FRA to these pumping data are shown in FIG. 6. This FRA plot 602 of pressure against flow rate forms a straight line. From the slope of this line, we calculate the mobility while pumping.

FRA is based on the following equation (Kasap et al., 1999):

$$P_i - P(t) = \frac{\mu}{kG_or_i}\left(V_{sys}c_t\frac{\partial P(t)}{\partial t} + q_{pm}\right),$$

where $P_i$, is the formation pressure, $G_o$ is the geometric factor, $r_i$, is the probe radius, $V_{sys}$ is the tool flowline volume, and the $q_{pm}$, is the pump rate. The fluid compressibility is calculated through multi-linear regression during the FRA analysis. Once the formation mobility ($k/\mu$) and the fluid bubble point pressure are known, the maximum pump rate can be calculated by the following equation:

$$q_{pm,max} = \frac{kG_or_i}{\mu}(P_i - P_b) - V_{sys}c_t\left(\frac{\partial P(t)}{\partial t}\right)_{P_b}.$$

Hence, the flowing pressure while pumping will stay above the bubble point pressure as long as the pump rate is below the maximum rate specified by the equation. FRA mobility while pumping is preferably updated periodically or in real time on each pump stroke because there can be mobility changes due to the fluid viscosity change or the formation permeability change (e.g., formation clean-up).

Figure 7:
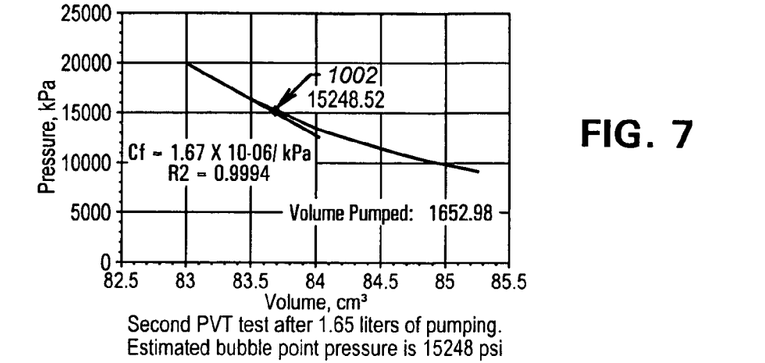
FIG. 7 is a plot of a second PVT test after 1.65 liters of pumping having an estimated bubble point pressure of 15,248 pounds per square inch (psi)
Figure 8:
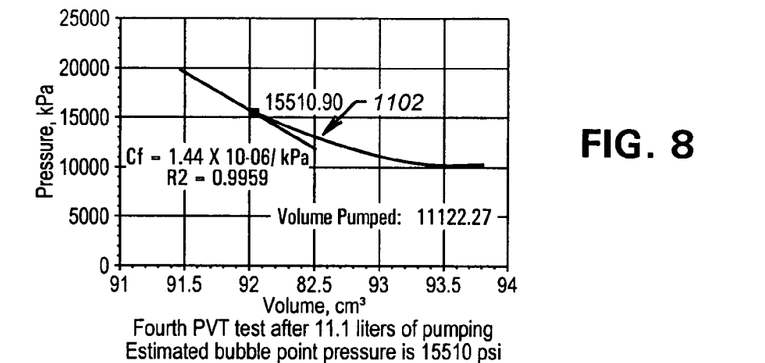
FIG. 8 is a plot of a fourth PVT test after 11.1 liters of pumping showing an estimated bubble point pressure of 15,510 psi.

A suitable wireline tool for use with the present invention is disclosed in U.S. Pat. No. 5,635,631 which is hereby incorporated by reference in its entirety. The present invention also enables low contamination sample detection and collection. In wells drilled using oil-based mud, successive downhole PV tests during pumping show increasing bubble point pressures as filtrate contamination is reduced. Hence, the degree of change from consecutive tests can be used as a formation clean-up indicator. FIG. 7 shows a pressure-volume plot 1002, which is the second of four tests. The test was performed after 1.65 liters of pumping and the estimated bubble point pressure is 15248 psi. FIG. 8 shows the fourth PV test results 1102 after 11.1 liters of pumping. The estimated bubble point pressure is 15510 psi. In these four tests, the first PV test shows a similar bubble point pressure as the second one, but the third test indicates 15377 psi. The increasing bubble point pressures estimated indicate that the sample contamination is still decreasing at the time of the fourth PVtest. When mud filtrate contamination decreases, the PV test's bubble point pressure increases because crude oil contains significant amounts of gas but filtrate does not.

The present invention also enables enhancing downhole PVT lab operations, referred to as $PVT^{MOD}$. The $PVT^{MOD}$ service, provided by Baker Atlas predicts downhole petroleum fluid PVT properties based on wire line formation tests and geochemistry reservoir fluid databases. The $PVT^{MOD}$ service was introduced to the formation sampling market in 2002 (Shammai et. al, 2002). The simulated PVT analysis is calculated from geochemical parameters and pressure gradients derived from formation pressure tests using the Baker Atlas RCI™ tool. The service brings the PVT lab downhole, with testing performed in-situ while tested fluids remain as close as possible to the true reservoir conditions.

In the $PV^{TMOD}$ system, formation pressure, temperature, and pressure gradient from the wireline formation tester are used as input along with three geochemical indicators (source rock aromaticity, thermal maturity, and biodegradation). $PV^{TMOD}$ provides estimated PVT properties, which are independent of mud contamination and available without the collection of physical samples. Often clients have to wait for the sample analysis results, which may take up to 6 to 8 weeks plus sample transport time. The predicted fluid properties enable clients to make timely decisions without waiting for the laboratory results.

Figure 9:
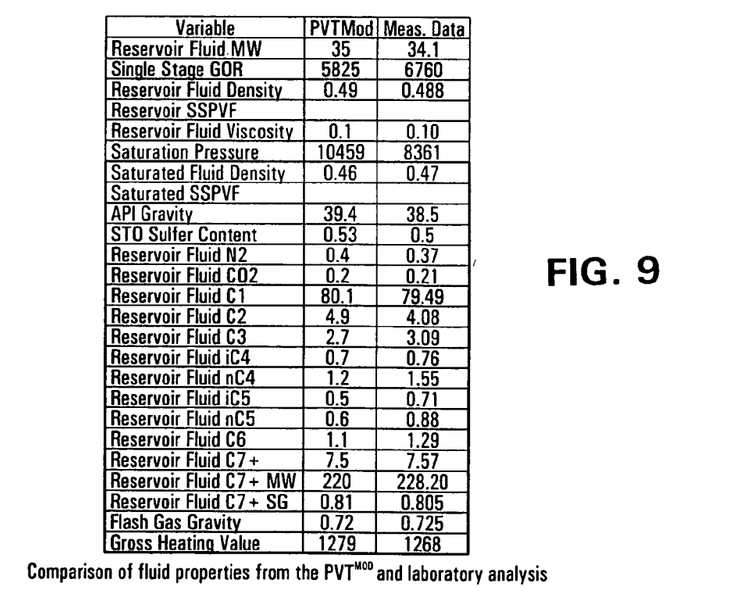
FIG. 9 provides a chart for comparison of fluid properties from the Baker Hughes Incorporated PVT$^{MOD}$ and laboratory analysis.
Figure 10:
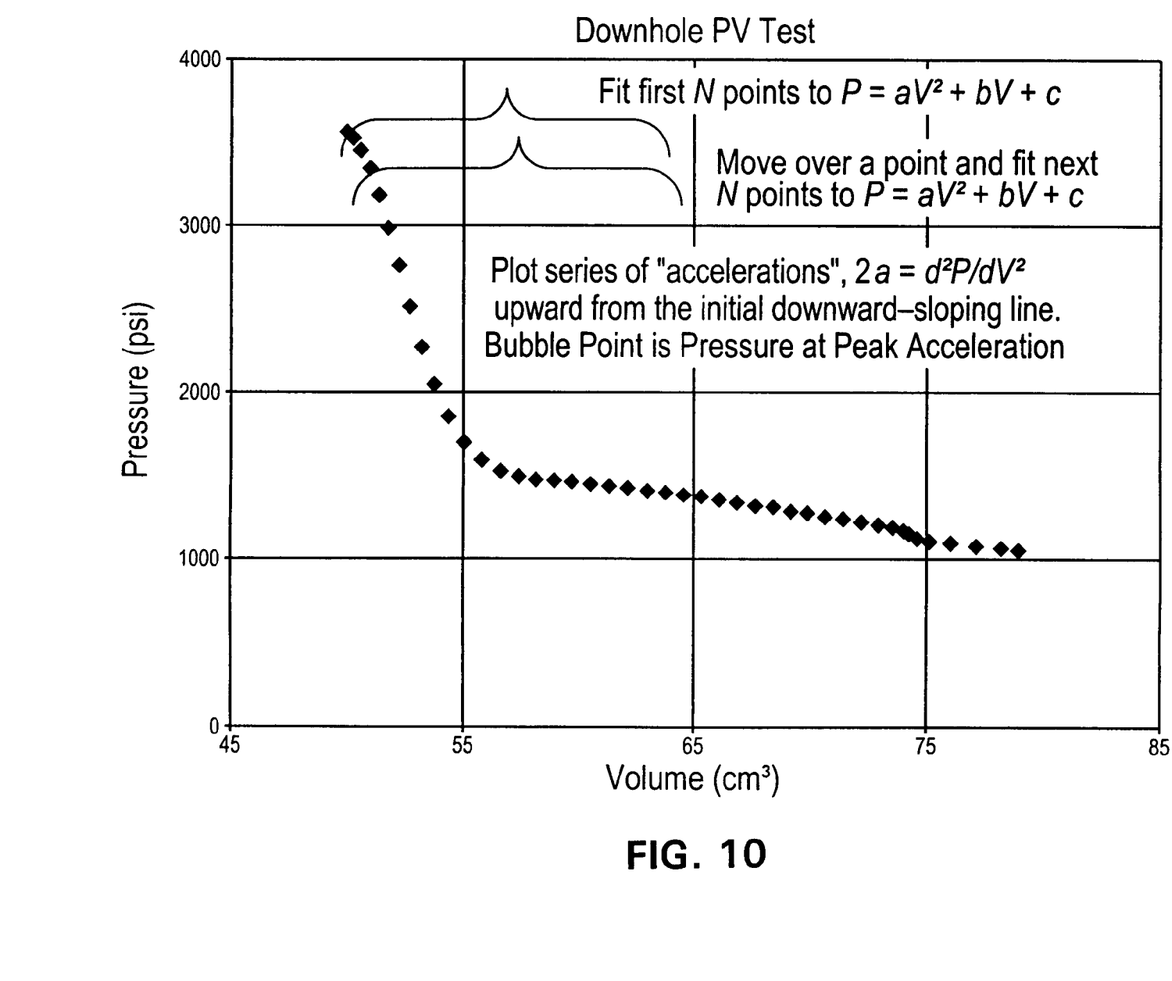
FIG. 10 is an illustration of the sliding average used in the present invention.

As shown in FIG. 9, the $PVT^{MOD}$ service predicted fluid properties are compared with the laboratory analysis results. Most computed PVT properties compare well except for the fluid saturation pressure. The saturation pressure prediction can be further improved once the PVT incorporates the mud gas data from the mud logging process. The saturation pressure from $PV^{TMOD}$ is compared with the downhole bubble point pressure measurement, performed by Baker Atlas RCI™ wireline tool, as an additional insight to the reservoir fluid phase behavior. FIG. 10 is an illustration of the sliding average used in the present invention.

As a quality control check, the present invention enables insuring that sample quality has not degraded in transit by comparing the bubble point pressure obtained downhole (just prior to pumping fluid into the tank) to the bubble point pressure obtained in the laboratory. When monetary or operational considerations preclude taking a large number of samples, downhole bubble point tests can be performed to determine whether fluid composition changes with depth.

Thus, the present invention provides a novel method and apparatus for finding bubble point pressure from P versus V data has been developed. The novel bubble point pressure determination method and apparatus is combined with determination of compressibility change method and visual inspection, which reduces the uncertainty in determining the bubble point pressure, $P_b$.

The present invention also enables obtaining downhole bubble point pressure and pumping mobility from FRA while pumping that insures that the sample has not undergone phase separation during pumping. The present invention further enables successive downhole PV tests which show increasing bubble point pressures with decreasing mud filtrate contamination because crude oil contains significant amounts of gas but filtrate does not.

Figure 11:
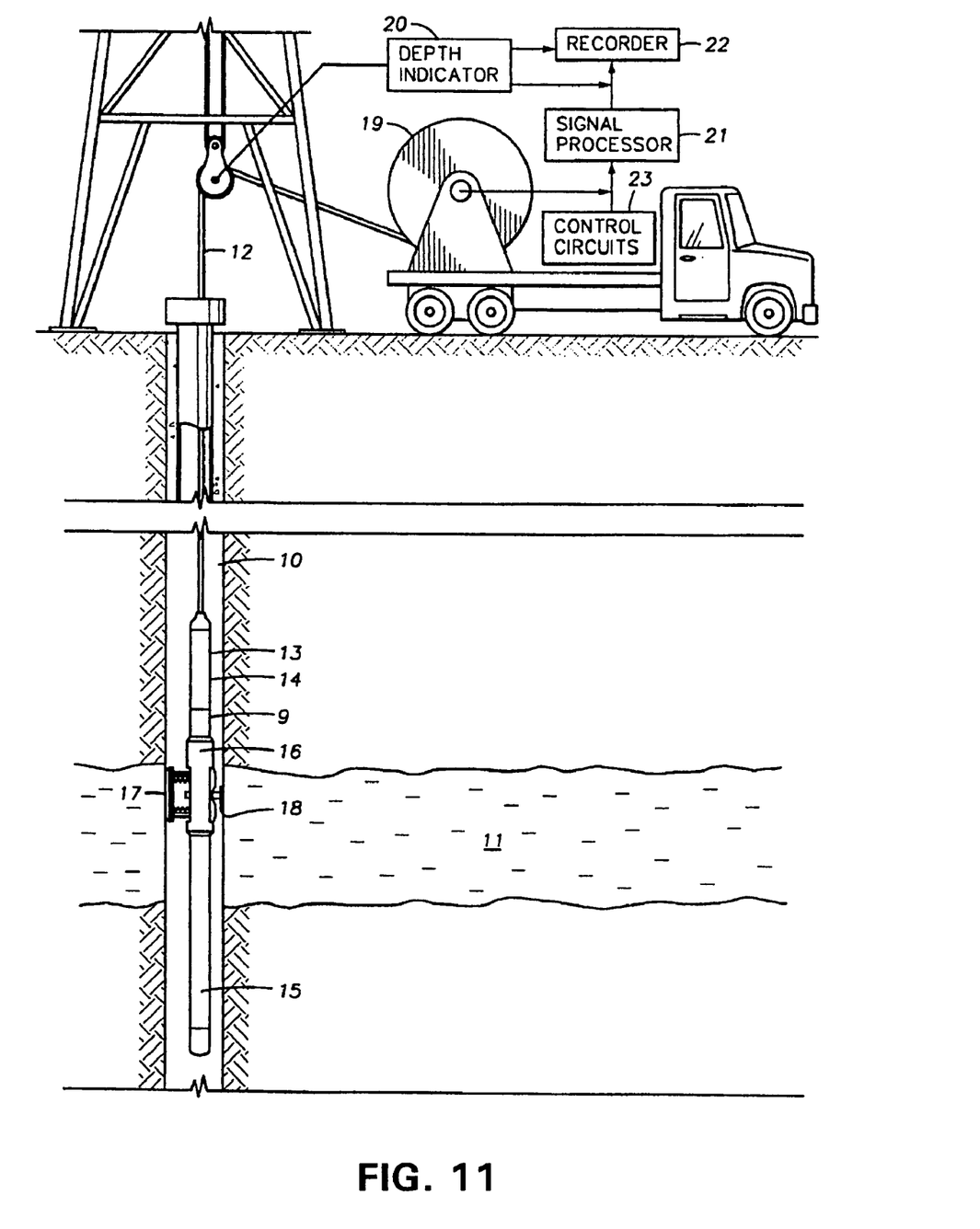
FIG. 11 is an illustration of the present invention in an operational environment down hole.

Turning now to FIG. 11, a wireline formation test tool is generally shown in FIG. 11 at 13. The tool 13 is attached to one end of an armored electrical cable 12 and is lowered into a wellbore 10 drilled through the earth. The cable 12 can be extended into the wellbore 10 by means of a winch 19 located at the earth's surface. The tool 13 comprises a back-up shoe and a mechanism for extending the shoe, shown generally at 17, which are disposed within a housing 16. The housing 16 also contains a tubular probe 18 which can be selectively extended and put into contact with the wall of the wellbore 10, as will be further explained. A sample tank 15 can be attached to the lower end of the housing 16 and can be selectively hydraulically connected to the probe 18 in order to store samples of fluids withdrawn from the earth. The probe 18, the back-up shoe 17 and selective valves (not shown) disposed within the housing 16 for operating the probe 18 and the shoe 17 can be of types familiar to those skilled in the art, and can receive hydraulic operating power from an hydraulic power unit 9 attached to the upper end of the housing 16.

The various operating functions of the tool 13, including extension of the shoe 17 and extension of the probe 18, can be controlled by the system operator entering command signals into control circuits 23 which are located at the earth's surface and are electrically connected to the cable 12, as is understood by those skilled in the art. The command signals can be decoded in an electronics unit/processor 14 disposed within the housing 16. As will be further explained, the tool 13 comprises sensors (not shown) for measuring pressure and volume within hydraulic lines (not shown in FIG. 11) connected to a sample chamber (not shown in FIG. 11). Measurements made by the sensors (not shown) are transmitted to the earth's surface as electrical signals generated by the electronics unit/processor 14. At the earth's surface the signals are decoded by a signal processor 21 which is also electrically connected to the cable 12. The decoded signals are reformatted into measurements which can be observed by the system operator and can be recorded by a recorder 22 connected to the signal processor 21. Electronics unit/processor 14 performs the calculations and determinations for bubble point, compressibility and other calculations regarding other fluid properties discussed above.

As the tool 13 is lowered into the wellbore 10, the depth at which the tool is located is indicated by a depth indicator 20 which is in contact with the cable 12 and measures the amount of cable 12 extended into the wellbore 10. When the tool 13 is determined to be positioned adjacent to a formation of interest, shown generally at 11, the system operator enters commands into the control circuits 23 to lock the tool 13 in position by extending the back-up shoe 17. The probe 18 is then extended, and withdrawal of a fluid sample can be initiated.

Figure 12:
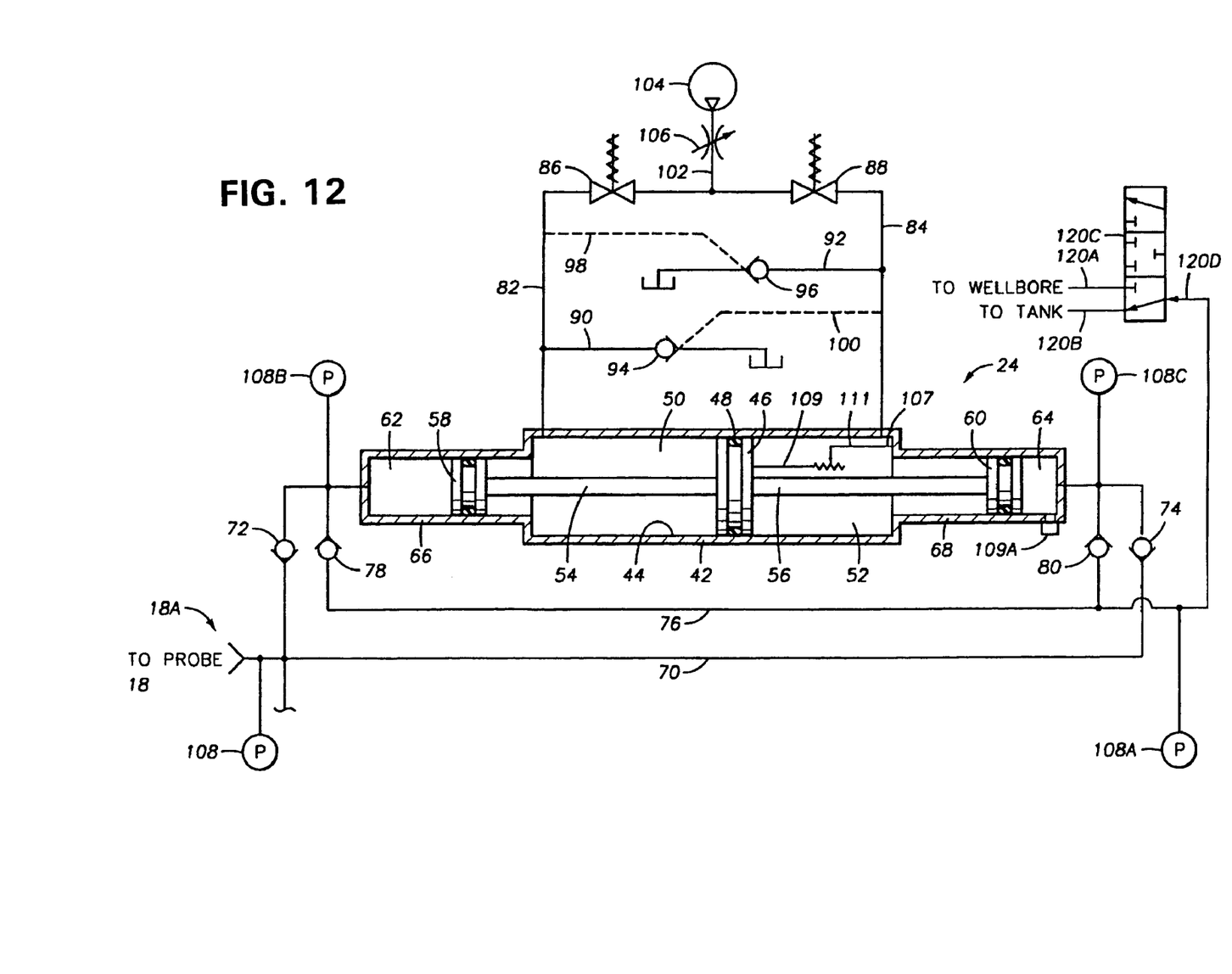
FIG. 12 is an illustration of a pump as used in the example of the present invention.
Figure 13A:
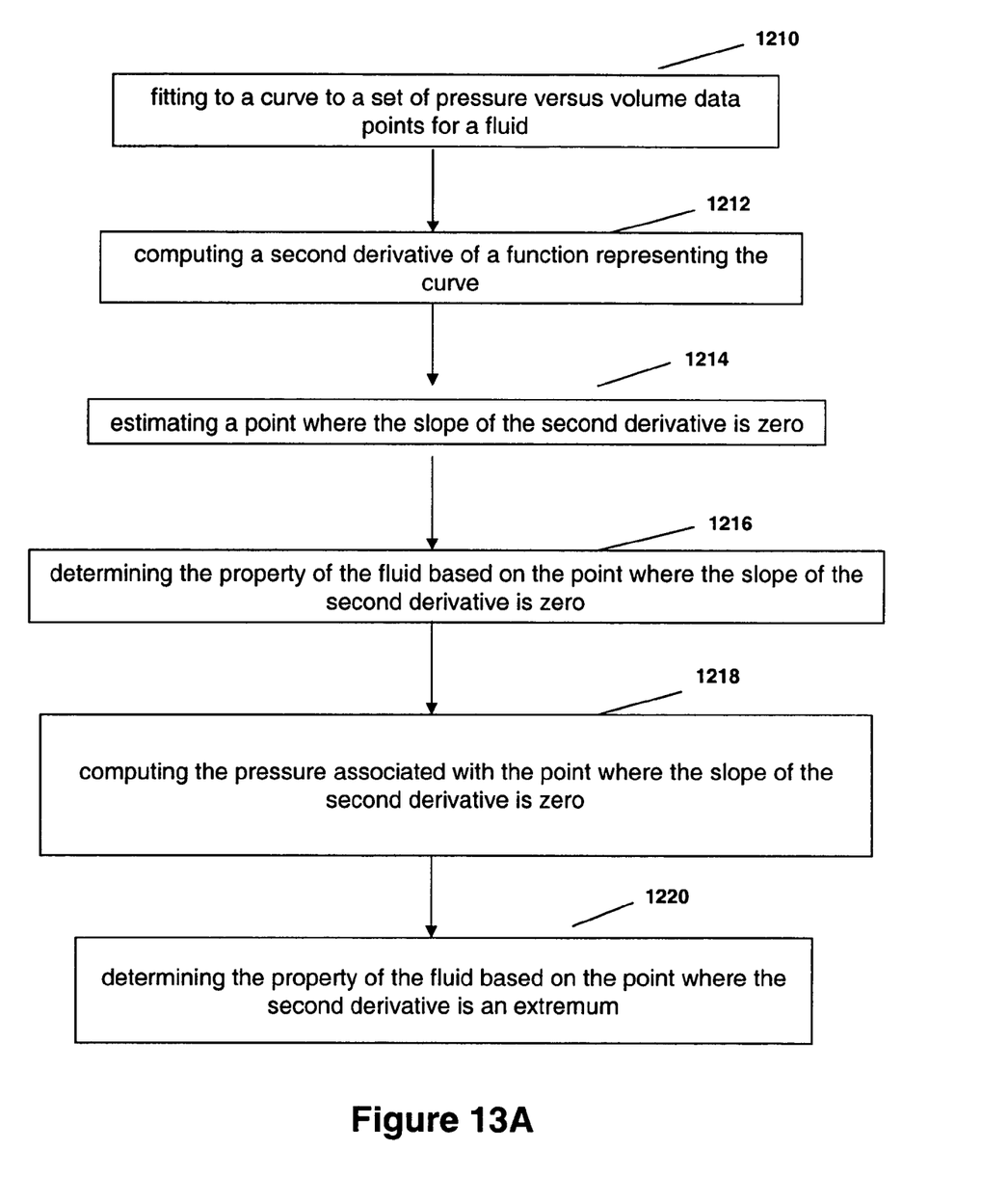
FIGS. 13A-13D comprise a chart of functions performed by the example of the present invention.
Figure 13B:
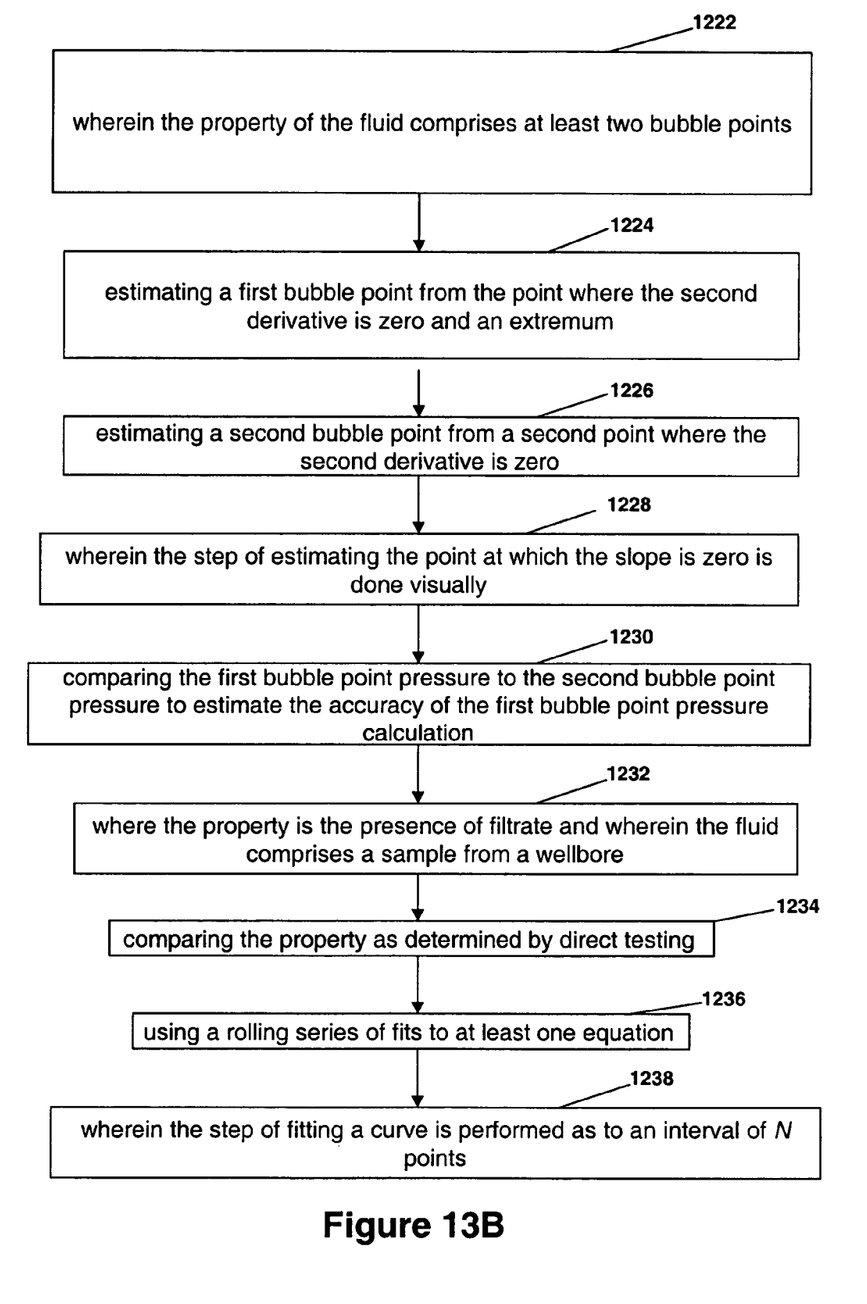
Figure 13C:
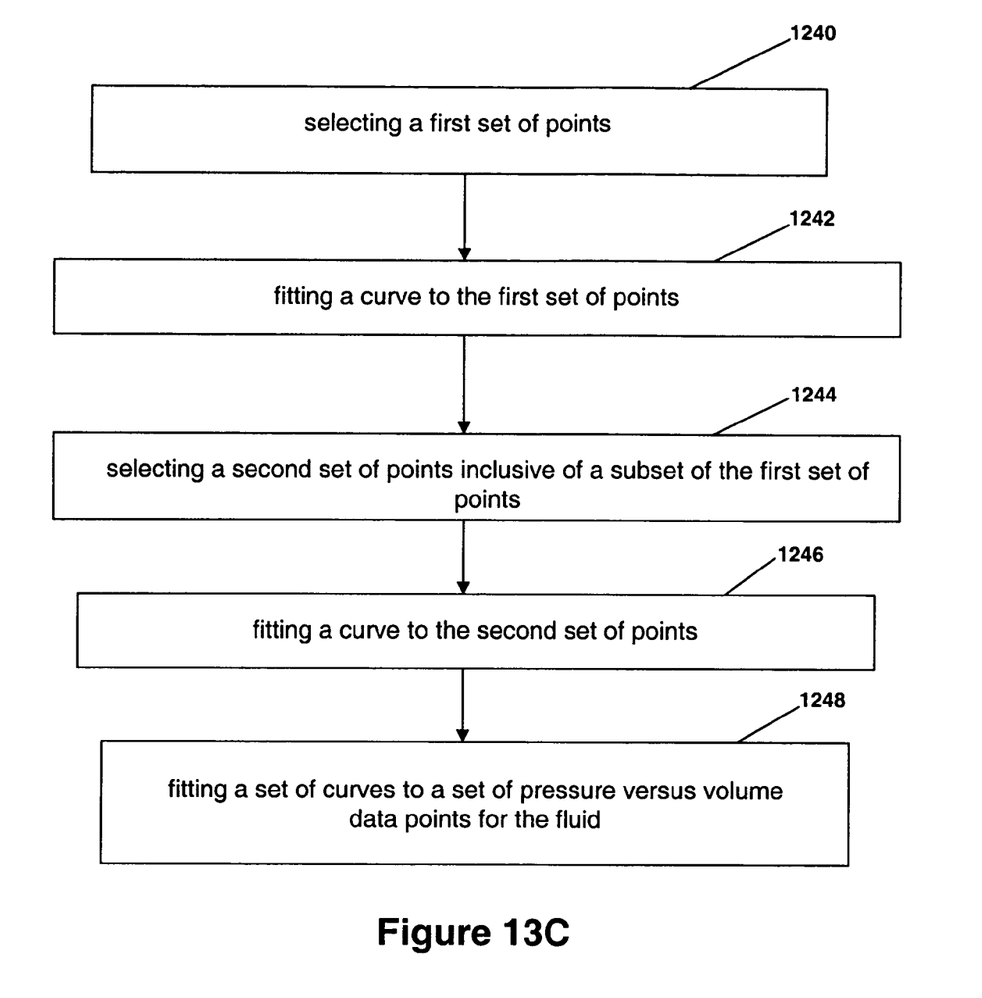
Figure 13D:
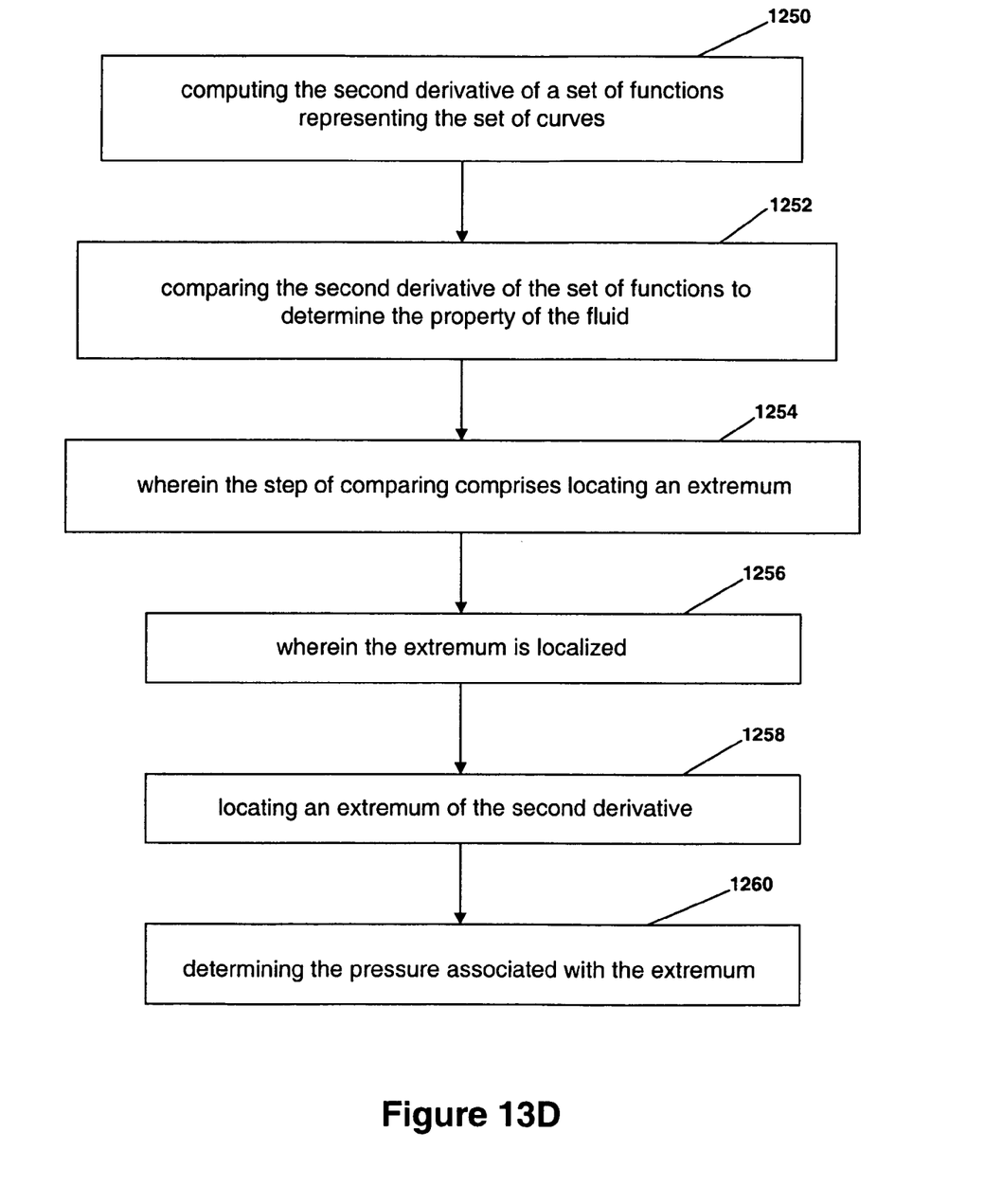

The means by which a fluid sample can be withdrawn from the formation of interest (11 in FIG. 11) can be better understood by referring to FIG. 12. A bi-directional, hydraulically powered pump, shown generally at 24, can controllably withdraw fluids through the probe (shown as 18 in FIG. 11). If so desired by the system operator, the pump 24 can further be used to discharge the fluids either into the sample tank (shown as 15 in FIG. 11) or into the wellbore (shown in FIG. 11 as 10).

The pump 24 comprises a drive cylinder 44, inside which is located a drive piston 46. The drive piston 46 is sealed against the inner wall of the drive cylinder 44 by an O-ring 48 or similar sealing device. The drive piston 46 is connected on one side to a first drive link 54, and on the other side is connected to a second drive link 56. The first drive link 54 is connected to one side of a first pumping piston 58. The second drive link 56 is similarly connected to a second pumping piston 60 disposed on the opposite side of the drive piston 46 to the first pumping piston 58. The first 58 and the second 60 pumping pistons are each respectively positioned within first 66 and second 68 pump cylinders disposed on opposite ends of the drive cylinder 44. Axial motion of the drive piston 46 is translated into equivalent axial motion of both the first 58 and second 60 pumping pistons, the significance of which will be further explained.

The drive piston 46 is moved axially by selective application of hydraulic pressure to either one side or to the other side of the drive piston 46. Hydraulic pressure is provided by a hydraulic pump 104 which is disposed in the hydraulic power unit (shown in FIG. 11 as 9). The hydraulic pump 104 is connected to a controllable pressure regulator 106 which provides the hydraulic pressure to move the drive piston 46. The discharge pressure from the regulator 106 can be controlled by the system operator entering appropriate commands into the control circuits (shown in FIG. 11 as 23). The controllable regulator discharge provides the system operator with a substantial degree of control over the rate at which the drive piston 46 moves since, as will be further explained, the drive piston 46 must overcome forces of fluid pressures acting on the pumping pistons 58, 60 in order to move.

The discharge from the regulator 106 is provided to hydraulic lines 102. The lines 102 connect to a first 86 and to a second 88 selective hydraulic valve. The selective valves 86, 88 can be operated by control signals sent from the control circuits (shown as 23 in FIG. 11) and decoded in the electronics unit/processor (shown at 14 in FIG. 11). The control signals provide operation of the valves 86, 88 in accordance with the pump 24 function selected by the system operator by entering appropriate commands into the control circuits 23, as will be further explained.

When the first valve 86 is opened, hydraulic pressure is applied through a first hydraulic control line 82 to a first chamber 50 in the drive cylinder 44, which is bounded at one end by the drive piston 46 and at the other end by the first pumping piston 58. The diameters of the first pump cylinder 66, and therefore, the first pumping piston 58 (and consequently their cross-sectional areas) are smaller than the diameter (and cross-sectional area) of the drive piston 46. Hydraulic pressure within the first drive chamber 50 therefore exerts more force on the drive piston 46 than on the first pumping piston 58, which causes motion of the drive piston 46, and all the previously described components that are attached to it, in the direction of the second pump cylinder 68. Hydraulic oil (not shown) is also present in a second drive chamber 52 disposed on the opposite side of the drive piston 46 and axially bounded by the drive piston 46 on one end and the second pumping piston 60 on the other end. As the drive piston 46 moves toward the second pump cylinder 68, the hydraulic oil in the second drive chamber 52 is displaced through a second hydraulic line 84 into a second discharge line 92 connected to a hydraulic oil supply tank (not shown) through a pilot operated check valve 96. The check valve 96 is held open by the operating hydraulic pressure from the line 102 applied through a control line 98 connected to the first hydraulic line 82. A similar, oppositely connected check valve, shown at 94, is connected through a control line 100 to the second hydraulic line 84, and as will be explained, vents the first hydraulic line 82 to the supply tank (not shown) when the drive piston 46 is moved in the opposite direction.

Motion of the drive piston 46 can be reversed by closing the first valve 86 and opening the second valve 88, thereby applying hydraulic pressure through the second hydraulic line 84 to the second drive chamber 52. The operation of the two valves 86, 88 can be performed automatically if the system operator instructs the control circuits 23 to operate the pump 24 continuously. The second pumping piston 60 can be substantially the same diameter as the first pumping piston 58, and thereby be smaller in diameter than the drive piston 46. Therefore hydraulic pressure applied to the second drive chamber 52 will cause motion of the drive piston 46 towards the first pump cylinder 66. As previously explained, the pressure on the second line 84 is also conducted through the control line 100 to open the pilot operated check valve at 94, which enables venting of the first drive chamber 50 to the supply tank (not shown).

Axial motion of the drive piston 46, which as previously explained is translated into equivalent axial motion of the first 58 and second 60 pumping pistons, results in corresponding changes in volume of a first 62 and of a second 64 pump chamber. The pump chambers 62, 64 can be selectively hydraulically connected to the probe 18 in order to withdraw fluid from the formation, as will be further explained.

A particular feature of the present invention which enables direct determination of the volume of the first 62 and the second 64 pump chambers is a displacement sensor, which in the present embodiment can be a linear potentiometer 111 disposed inside the drive cylinder 44 and connected by a link 109 to the drive piston 46. Axial motion of the drive piston 46 results in directly corresponding change in the resistance of the potentiometer 111 as applied to a signal line 107. The resistance as applied to the signal line 107 is converted into a corresponding signal in the electronics unit/processor (shown in FIG. 11 as 14), which signal can be decoded the electronics unit/processor 14 or in the signal processor (shown as 21 in FIG. 11) and converted into a measurement of the position of the drive piston 46, and thereby the exact volume of either pump chamber 62, 64, since the axial motion of all three pistons 46, 58, 60 is equivalent. It is contemplated that other means for measuring the axial position (and thereby the volume of the pumping chambers 62, 64) of the drive piston 46 or of the first 58 or second 60 piston can be employed, for example an acoustic travel time sensor disposed within either drive chamber 50 or 52. The linear potentiometer 111 of the present invention is used only as a matter of convenience and should not be construed as an explicit limitation on the means for determining the volume of the pumping chambers 62, 64.

Temperature within the second pumping chamber 64 can be measured by a temperature sensor 109A. The temperature sensor 109A can be of a type known in the art which is operable at very high pressures. Alternatively, the temperature sensor 109A can be connected to a fluid line which connects check valves (shown at 80 and 74) to the second pumping chamber 64. The check valves will be further explained. It is to be understood that the temperature sensor 109A can also be connected to the first pumping chamber 62. The selection of the pumping chamber to which to connect the temperature sensor 109A is only a matter of convenience for the system designer. As is understood by those skilled in the art, the temperature sensor 109A can be of a type which generates an electrical signal corresponding to the temperature to which the sensor 109A is exposed. The electrical signal from the sensor 109A can be conducted to the electronics unit 14 for transmission to the recorder 22. The use of the measurements made by the temperature sensor 109A will be further explained.

Another advantageous feature of the present invention is that the rate of movement of the drive piston 46 can be controlled by the system operator. As previously explained, the drive piston 46 must exert force sufficient to overcome opposing force caused by the formation (shown as 11 in FIG. 11) fluid pressure in the pumping chambers 62, 64 acting on their respective pumping pistons 58, 60 in order to move. The amount of hydraulic pressure applied to the drive piston 46 is controllable by the system operator through the regulator 106. It is therefore possible to operate the drive piston 46 at a hydraulic pressure which just overcomes the formation fluid pressures acting on the pumping pistons 58, 60, in which case the drive piston 46 will move extremely slowly. Moving the drive piston 46 very slowly reduces the possibility, among others, that subtle changes in a relationship between the volume of the pumping chambers 62, 64 and the fluid pressure will go undetected.

When withdrawal of a sample from the formation (shown at 11 in FIG. 11) is begun, the drive piston 46 is typically positioned so that either the first 58 or the second 60 pumping piston is fully extended into its respective pumping chamber 62 or 64. Withdrawal of a sample is begun by application of hydraulic pressure to the appropriate drive chamber 50 or 52 (adjacent to the completely compressed pump chamber into which its pump piston 58 or 60 is fully extended), whereupon the drive piston 46 moves and correspondingly displaces the pumping pistons 58, 60, thereby increasing the volume of the fully compressed pumping chamber 62 or 64.

The first 62 and second 64 pumping chambers are connected, respectively to a first 72 and a second 74 inlet check valve, both of which enable flow from the probe (shown as 18 in FIG. 11) into an inlet flowline 70 (connected as shown at 18A to the probe 18) on the expansion stroke of the respective pumping chamber 62 or 64. The inlet flowline 70 is further connected to a highly precise pressure transducer 108 (which is itself connected to the electronics unit/processor 14) which enables substantially continuous measurement of the pressure in the flowline 70. The use of the pressure measurement made by the transducer 108 in the present invention will be further explained.

During the discharge stroke on one chamber 62 or 64, corresponding to an expansion stroke in the opposing chamber 64 or 62, discharge from the compressing chamber 62 or 64 is conducted, respectively, through a first 78 and second 80 discharge check valve into a discharge line 76. The discharge line 76 can be selectively hydraulically connected to the sample tank (shown in FIG. 11 as 15), vented to the wellbore (shown in FIG. 11 as 10), or the discharge line 76 can be hydraulically closed at its end. Selective connection of the discharge line 76 can be performed by a four-way solenoid operated valve as shown at 120. The solenoid can operate in response to commands entered into the control circuits (23 in FIG. 11) by the system operator. Operating the solenoid can cause a common port 120D on the valve 120 to be connected to a first selective port 120A which is vented to the wellbore 10, to a second selective port 120B connected to the sample tank 15, or to a third selective port 120C which is closed.

If the system operator desires, for example, to fill the sample tank 15 with fluid withdrawn through the probe 18, the pump 24 can be operated continuously until the tank 15 is filled by automatic selective operation of the valves 86, 88 and 120. Automatic valve control can be performed by the control circuits (shown in FIG. 11 as 23).

A second pressure transducer shown at 108A can be hydraulically connected to the discharge line 76 at a connection position before the common port 120A on the four way valve 120. The purpose of the second transducer 108A will be further explained.

The means by which fluid samples can be controllably withdrawn from the earth formation of interest (11 in FIG. 11) having been described, the method of the present invention by which fluids can be characterized as explained above.

As previously described herein, a sample can be withdrawn into the inlet line (shown as 70 in FIG. 12) by the pump (shown in FIG. 12 as 24). Tests can be performed on a part of the fluid sample which is withdrawn through the inlet line 70 and into the one of the pumping chambers (shown as 62 and 64 in FIG. 12) which is on its intake stroke. Testing the sample is initiated by the system operator entering a command into the control circuits (23 in FIG. 11) to operate the four way valve (120 in FIG. 12) so as to hydraulically close the discharge line (76 in FIG. 12). Closing the discharge line 76 traps the sample within a controllable volume. The controllable volume includes the volume of the one pumping chamber (62 or 64) in which the fluid is being drawn, and the discharge line 76 as far as the four-way valve 120.

Testing can continue, as will be explained, by operating the pump 24 in the reverse direction as previously described herein so as to expand the volume of the fluid sample. While the sample is being expanded, the pressure can be observed by the system operator. As previously described herein, the pressure in the discharge line 76 is measured by the second transducer (108A in FIG. 12).

Turning now to FIGS. 13A-D, a flow chart showing functions performed electronics unit/processor 14 and associated method and apparatus in the present example of the invention is depicted. The functions are not necessarily performed in the order shown in FIGS. 13A-13D. As shown in block 1210 the present invention performs a function for fitting a curve to a set of pressure versus volume data points for a fluid. In block 1212 the present invention performs a function for computing a second derivative of a function representing the curve. In block 1214 the present invention performs a function for estimating a point where the slope of the second derivative is zero.

In block 1216 the present invention performs a function for determining the property of the fluid based on the point where the slope of the second derivative is zero. In block 1218 the present invention performs a function for computing the pressure associated with the point where the slope of the second derivative is zero. In block 1220 the present invention performs a function for determining the property of the fluid based on the point where the second derivative is an extremum. In block 1222 the present invention performs a function wherein the property of the fluid comprises at least two bubble points, the method further comprising estimating a first bubble point from the point where the second derivative is zero and an extremum. In block 1224 the present invention performs a function for estimating a second bubble point from a second point where the second derivative is zero.

In block 1226 the present invention performs a function wherein the step of estimating the point at which the slope is zero is done visually. In block 1228 the present invention performs a function for comparing the first bubble point pressure to the second bubble point pressure to estimate the accuracy of the first bubble point pressure calculation. In block 1230 the present invention performs a function wherein the property is the presence of filtrate and wherein the fluid comprises a sample from a wellbore. In block 1232 the present invention performs a function for comparing the property the property as determined by direct testing.

In block 1234 the present invention performs a function for using a rolling series of fits to at least one equation. In block 1236 the present invention performs a function wherein the step of fitting a curve is performed as to an interval of N points In block 1238 the present invention performs a function for selecting a first set of points. In block 1240 the present invention performs a function for fitting a curve to the first set of points. In block 1242 the present invention performs a function for selecting a second set of points inclusive of a subset of the first set of points. In block 1244 the present invention performs a function for fitting a curve to the second set of points. In block 1246 the present invention performs a function for fitting a set of curves to a set of pressure versus volume data points for the fluid. In block 1248 the present invention performs a function for computing the second derivative of a set of functions representing the set of curves. In block 1250 the present invention performs a function for comparing the second derivative of the set of functions to determine the property of the fluid. In block 1252 the present invention performs a function wherein the step of comparing comprises locating an extremum. In block 1252 the present invention performs a function wherein the extemum is localized. In block 1254 the present invention performs a function wherein the property is a bubble point and wherein the step of comparing comprises locating an extremum of the second derivative. In block 1256 the present invention performs a function for determining the pressure associated with the extremum.

In another embodiment, the method of the present invention is implemented as a set computer executable of instructions on a computer readable medium, comprising ROM, RAM, CD ROM, Flash or any other computer readable medium, now known or unknown that when executed cause a computer to implement the method of the present invention.

While the foregoing disclosure is directed to the exemplary embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

The invention claimed is:

1. A method for estimating a property of a fluid comprising:
   fitting a curve to pressure and volume data points for a fluid obtained using a downhole tool;
   computing a second derivative of pressure with respect to volume from the curve;
   estimating the property of the fluid at a point where slope of the second derivative is zero; and
   storing a value of the estimated property of the fluid in a suitable medium.

2. The method of claim 1, wherein the property of the fluid comprises a bubble point.

3. The method of claim 2, wherein estimating the property of the fluid further comprises computing pressure associated with the point where the slope of the second derivative is zero.

4. The method of claim 2, wherein estimating the property of the fluid is based on the point where the second derivative is an extremum.

5. The method of claim 1, wherein the property of the fluid comprises at least two bubble points, the method further comprising:
   estimating a first bubble point from the point where the second derivative is zero and an extremum; and
   estimating a second bubble point from a second point where the second derivative is zero.

6. The method of claim 5 further comprising:
   comparing the first bubble point to the second bubble point to estimate accuracy of the first bubble point estimation.

7. The method of claim 1, wherein estimating the property of the fluid at the point where the slope is zero is performed by a processor.

8. The method of claim 1 wherein the property of the fluid is presence of a filtrate and wherein the fluid comprises a sample from a wellbore.

9. The method of claim 1 further comprising:
comparing the property of the fluid with a property determined by direct testing of the fluid.

10. The method of claim 1 wherein fitting a curve further comprises:
using a rolling series of fits to at least one equation.

11. The method of claim 1 wherein fitting a curve further comprises:
selecting a first set of points;
fitting a curve to the first set of points;
selecting a second set of points inclusive of a subset of the first set of points; and
fitting a curve to the second set of points.

12. The method of claim 1 wherein volume data points are derived from a piston movement.

13. The method of claim 1 wherein fitting a curve is performed as to an interval of N points.

14. A method for estimating a property of a fluid comprising:
fitting a set of curves to data selected for one of pressure and volume, pressure and temperature, and volume and temperature for the fluid obtained using a downhole tool;
computing a second derivative relating to the selected one of pressure and volume, pressure and temperature, and volume and temperature from each curve in the set of curves;
comparing the computed second derivatives to estimate the property of the fluid; and
storing an estimated value of the property of the fluid in a suitable medium.

15. The method of claim 14 wherein comparing comprises locating an extremum.

16. The method of claim 15 wherein the extremum is localized.

17. The method of claim 14 wherein the property of the fluid is a bubble point and wherein comparing comprises:
locating an extremum of the second derivative; and
determining the pressure associated with the extremum.

18. A compute-readable medium containing instructions that when executed by a computer perform a method for estimating a property of a fluid comprising:
fitting a curve to data points for a selected one of pressure and volume, pressure and temperature and, volume and temperature for the fluid obtained using a downhole tool;
computing a second derivative relating to the selected one of pressure and volume, pressure and temperature, and volume and temperature from the fitted curve;
estimating the property of the fluid at a point where the slope of the second derivative is zero; and
storing a value of the estimated property of the fluid in a suitable medium.

19. The computer-readable medium of claim 18 wherein the property of the fluid is a bubble point, and wherein the method further comprises:
estimating the property of the fluid where the slope of the second derivative is zero.

20. The computer-readable medium of claim 19 wherein estimating the property of the fluid comprises:
computing a pressure associated with the point where the slope of the second derivative is zero.

21. The computer-readable medium of claim 18 wherein the property of the fluid comprises at least two bubble points, and wherein the method further comprises:
estimating a first bubble point from the point where the second derivative is zero and an extremum; and
estimating a second bubble point from a second point where the second derivative is zero.

22. A computer-readable medium containing instructions that when executed by a computer perform a method for estimating a property of a fluid comprising:
fitting a set of curves to data points for a selected one of pressure and volume, pressure and temperature, and volume and temperature for the fluid obtained using a downhole tool;
computing a second derivative relating to the selected one of pressure and volume, pressure and temperature, and volume and temperature from each curve in the set of curves;
comparing the computed second derivatives to estimate the property of the fluid; and
storing a value of the property of the fluid in a suitable medium.

23. The computer-readable medium of claim 22 wherein comparing comprises locating an extremum.

24. The computer-readable medium of claim 23 wherein the extremum is localized.

25. The computer-readable medium of claim 22 wherein the property is a bubble point and wherein the step of comparing comprises:
locating an extremum of the second derivative; and
determining a pressure associated with the extremum.

26. An apparatus for estimating a property of a fluid comprising:
a sensor unit for measuring at least two of a set consisting of pressure, volume and temperature of the fluid downhole;
a processor programmed to fit a curve to data points for a selected one of pressure and volume, pressure and temperature, and volume and temperature for the fluid;
compute a second derivative relating the selected one of pressure and volume, pressure and temperature and volume and temperature from the curve;
estimate the property of the fluid at a point where the slope of the second derivative is zero; and
store a value of the estimated parameter of the fluid in a suitable medium.

27. The apparatus of claim 26 further comprising an output device that comprises at least one of the set consisting of a printer, cathode ray tube, and visual display.

28. The apparatus of claim 26 further comprising:
a wireline tool comprising a fluid collector and sensor unit in data communication with the processor.

29. The apparatus of claim 28 wherein the wireline tool is a member of a set consisting of a) a sampling tool and b) a testing tool.

* * * * *